(12) United States Patent
Hoehn et al.

(10) Patent No.: US 8,877,040 B2
(45) Date of Patent: Nov. 4, 2014

(54) HYDROTREATING PROCESS AND APPARATUS RELATING THERETO

(75) Inventors: Richard Hoehn, Mt. Prospect, IL (US); Soumendra Mohan Banerjee, New Delhi (IN); Dave Bowman, Cary, IL (US); Xin X. Zhu, Long Grove, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/589,960

(22) Filed: Aug. 20, 2012

(65) Prior Publication Data

US 2014/0048447 A1    Feb. 20, 2014

(51) Int. Cl.
*C10G 49/22*    (2006.01)
*C07C 7/12*    (2006.01)
*B01D 3/00*    (2006.01)
*C10G 47/00*    (2006.01)

(52) U.S. Cl.
CPC . *C10G 49/22* (2013.01); *C07C 7/12* (2013.01); *B01D 3/00* (2013.01); *C10G 47/00* (2013.01)
USPC ............... 208/102; 208/310 R; 208/363

(58) Field of Classification Search
USPC ....... 208/99, 104, 107, 100, 102, 310 R, 347, 208/355, 356, 360; 203/71, 72, 76, 78, 79, 203/81, 82, 83, 84, 89, 97, 98
See application file for complete search history.

(56) References Cited

U.S. PATENT DOCUMENTS

| | | | |
|---|---|---|---|
| 3,130,006 A | 4/1964 | Rabo et al. | |
| 3,316,958 A | 5/1967 | Johnston | |
| 4,160,692 A | 7/1979 | Mitchell et al. | |
| 4,173,246 A | 11/1979 | Nunlist et al. | |
| 4,363,718 A | 12/1982 | Klotz | |
| 4,447,315 A | 5/1984 | Lamb et al. | |
| 4,698,146 A | 10/1987 | Gruia | |
| 5,120,427 A | 6/1992 | Stine et al. | |
| 5,139,646 A * | 8/1992 | Gruia | 208/99 |
| 5,230,217 A | 7/1993 | Agrawal et al. | |
| 5,580,442 A | 12/1996 | Kwon et al. | |
| 5,720,872 A * | 2/1998 | Gupta | 208/57 |
| 5,849,979 A | 12/1998 | Kalnes et al. | |
| 6,146,520 A | 11/2000 | Gupte et al. | |
| 6,190,535 B1 | 2/2001 | Kalnes et al. | |
| 6,361,683 B1 | 3/2002 | Kalnes | |
| 6,372,122 B1 | 4/2002 | Gorman | |
| 6,379,532 B1 | 4/2002 | Hoehn et al. | |
| 6,379,533 B1 | 4/2002 | Thakkar et al. | |

(Continued)

FOREIGN PATENT DOCUMENTS

WO    2011043904 A1    4/2011
WO    2012052116    4/2012

OTHER PUBLICATIONS

U.S. Appl. No. 12/967,793, filed Dec. 14, 2010, Hoehn et al.
U.S. Appl. No. 12/967,792, filed Dec. 14, 2010, Hoehn et al.
U.S. Appl. No. 13/365,210, filed Feb. 2, 2012, Van Wees.
Hunter et al, "New Process for Controlling Heavy Poly-Nuclear Aromatics (HPNA) in a Hydrocracker", American Fuel & Petrochemical Manufacturers Annual Meeting Paper, Mar. 2012, pp. 16 Pages.

(Continued)

*Primary Examiner* — Prem C Singh
*Assistant Examiner* — Brandi M Doyle
(74) *Attorney, Agent, or Firm* — James C Paschall

(57) ABSTRACT

One exemplary embodiment can be a process for treating a hydroprocessing fraction. The process can include obtaining a bottom stream from a fractionation zone, and passing at least a portion of the bottom stream to a film generating evaporator zone for separating a first stream containing less heavy polynuclear aromatic compounds than a second stream.

6 Claims, 5 Drawing Sheets

(56) References Cited

U.S. PATENT DOCUMENTS

| | | | |
|---|---|---|---|
| 6,379,535 | B1 | 4/2002 | Hoehn et al. |
| 6,858,128 | B1* | 2/2005 | Hoehn et al. ............... 208/111.3 |
| 6,974,535 | B2 | 12/2005 | Cody et al. |
| 7,588,678 | B2 | 9/2009 | Barthelet et al. |
| 2009/0050524 | A1 | 2/2009 | Kim et al. |
| 2010/0326887 | A1* | 12/2010 | McGehee et al. ............ 208/107 |
| 2012/0145513 | A1 | 6/2012 | Hoehn et al. |

OTHER PUBLICATIONS

Latif, "Polynuclear Aromatic Formation in Hydrocracker and Their Impact on Catalyst Stability", Studies in Surface Science and Catalysis . . . Catalysts in Petroleum Refining 1989, 1990, vol. 53, pp. 349-361.

Search Report dated Dec. 19, 2013 for corresponding PCT application.

* cited by examiner

HYDROTREATING PROCESS AND APPARATUS RELATING THERETO

FIELD OF THE INVENTION

This invention generally relates to a process and apparatus for hydrotreating.

DESCRIPTION OF THE RELATED ART

Often, heavy polynuclear aromatic (may be abbreviated as "HPNA") compounds may be a secondary product from a hydrocracking process. The HPNA compounds can be a problem particularly for high conversion hydrocracking units, and be present in the reactor product. Recycling unconverted oil to increase yields of distillate product can result in an accumulation of HPNA compounds in the unconverted oil. Accumulated HPNA compounds in the recycle oil may deposit on the catalyst as coke, which may degrade catalyst performance and result in shorter catalyst cycle length. Production of undesired HPNA compounds can be more pronounced for hydrocracking units processing heavier feeds. Thus, it would be desirable to remove the HPNA compounds from the unconverted oil so as to minimize the catalyst deactivation. One option is to lower conversion by bleeding a portion of the unconverted oil to remove accumulated HPNA compounds. Unfortunately, this is often undesirable due to economic and logistic considerations because of yield loss and lack of market for the unconverted oil. Thus, there is a desire to provide an improved process that provides improved performance and prevents HPNA compounds accumulation without the shortcomings discussed above.

SUMMARY OF THE INVENTION

One exemplary embodiment can be a process for treating a hydroprocessing fraction. The process can include obtaining a bottom stream from a fractionation zone, and passing at least a portion of the bottom stream to a film generating evaporator zone for separating a first stream containing less heavy polynuclear aromatic compounds than a second stream.

Another exemplary embodiment may be a process for treating a hydroprocessing fraction. The process may include obtaining a bottom stream from a fractionation zone, passing at least a portion of the bottom stream to a first stripping zone, sending a first portion of the stripped bottom stream to an adsorption zone, and sending a second portion of the stripped bottom stream to a second stripping zone.

A further exemplary embodiment can be an apparatus for hydroprocessing. The apparatus may include a hydroprocessing zone, a fractionation zone communicating with the hydroprocessing zone for receiving a hydroprocessed fraction, a first stripping zone communicating with the fractionation zone for receiving a bottom stream, and a second stripping zone communicating with the first stripping zone for receiving at least a portion of a stripped stream from the first stripping zone.

The embodiments disclosed herein can remove HPNA compounds from the unconverted oil by using a film generating evaporator zone to evaporate all but the heaviest portions of the unconverted oil. Generally, the undesirable HPNA compounds are contained largely in the unevaporated liquid. This material can be removed from the apparatus, but many fractionators do not have a sufficient number of trays in the column, which can result in poor fractionation. The resulting diesel product produced from the fractionator may have poor cold flow properties, as heavier components from the unconverted oil can be present in the diesel product. Furthermore, poor fractionation can result in a great loss of gas oil or diesel range materials into the unconverted oil or the bottom product of fractionators. Utilizing stripping steam may improve the separation between gas oil and bottom product using steam as the stripping medium for better recovery of gas oil, but the existing number of trays generally limit the effectiveness of stripping steam.

Furthermore, a film generating evaporator zone can include a wiped film evaporator to remove additional HPNA compounds. When a stripping column is added to the wiped film evaporator, this exemplary embodiment can recover gas oil for improved yield while removing extra HPNA compounds. In another exemplary embodiment, two stripping vessels can be used with one stripping vessel used for extra gas oil recovery and the other for removal of HPNA compounds. In yet another exemplary embodiment, a compact two-stripping vessel design can be employed featuring a split-wall column with one side performing bottom stripping and the other side stripping of HPNA compounds.

DEFINITIONS

As used herein, the term "stream" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 . . . Cn where "n" represents the number of carbon atoms in the one or more hydrocarbon molecules. Furthermore, a superscript "+" or "−" may be used with an abbreviated one or more hydrocarbons notation, e.g., $C3^+$ or $C3^-$, which is inclusive of the abbreviated one or more hydrocarbons. As an example, the abbreviation "$C3^+$" means one or more hydrocarbon molecules of three carbon atoms and/or more.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "rich" can mean an amount of at least generally about 50%, and preferably about 70%, by mole, of a compound or class of compounds in a stream.

As used herein, the term "substantially" can mean an amount of at least generally about 80%, preferably about 90%, and optimally about 99%, by mole, of a compound or class of compounds in a stream.

As used herein, the term "hydroprocessing" can refer to a process utilizing hydrogen to treat one or more hydrocarbons. Hydroprocessing can include hydrocracking, hydrodemetallization, hydrotreating, hydrodewaxing, hydroisomerization, and/or aromatic hydrotreating. As an example, hydrocracking can refer to a process for cracking hydrocarbons in the presence of hydrogen, and optionally a catalyst, to lower molecular weight hydrocarbons. As a further example, hydrotreating can refer to a process that removes heteroatoms, such as sulfur, nitrogen, and metals from a hydrocarbon feedstock by contacting hydrocarbons with hydrogen in the presence of a suitable catalyst. Hydrotreating can also saturate hydrocarbons with double and triple bonds as well as aromatics. Aromatic hydrotreating may also be specifically designed to saturate aromatics.

As used herein, the term "heavy polynuclear aromatics" may be abbreviated "HPNA" and can characterize compounds having eleven or more "benzene rings" typically produced in a hydrocracking reaction zone. Such heavy polynuclear aromatics may also be referred to as polynuclear aromatics.

As used herein, the term "fluid" can mean one or more gases, one or more liquids, and/or one or more vapors.

As used herein, the term "gas" can mean a single gas or a solution of a plurality of gases.

As used herein, the term "liquid" can mean a single liquid, or a solution or a suspension of one or more liquids with one or more gases and/or solid particles.

As used herein, the term "vapor" can mean a gas or a dispersion that may include or consist of one or more hydrocarbons and/or water. A dispersion may include one or more of a gas, a liquid, and a solid, such as a dispersion of an aerosol and/or a fog.

As used herein, the term "top" can be at or near the top of a vessel.

As used herein, the term "bottom" can be at or near the bottom of a vessel.

As used herein, the term "non-distillable component" can include finely divided particulate matter that can tend to foul hot heat exchange surfaces, form coke on catalyst, deactivate catalyst, and/or plug catalyst beds. Generally, the finely divided particulate matter can include polymerized organic matter.

As used herein, the term "kilopascal" may be abbreviated "KPa" and all pressures disclosed herein are absolute; the term "hour" may be abbreviated "hr"; the term "kilogram" may be abbreviated "kg"; the term "meter-cubed" may be abbreviated "$m^3$"; and the term "liquid hourly space velocity" may be abbreviated "LHSV".

As used herein, a boiling point may be determined by ASTM Method D2887-97, unless another method is specified.

As depicted, process flow lines in the figures can be referred to interchangeably as, e.g., lines, pipes, feeds, distillates, condensates, remainders, mixtures, portions, hydrocarbons, effluents, products, or streams.

DETAILED DESCRIPTION

Figure 1:
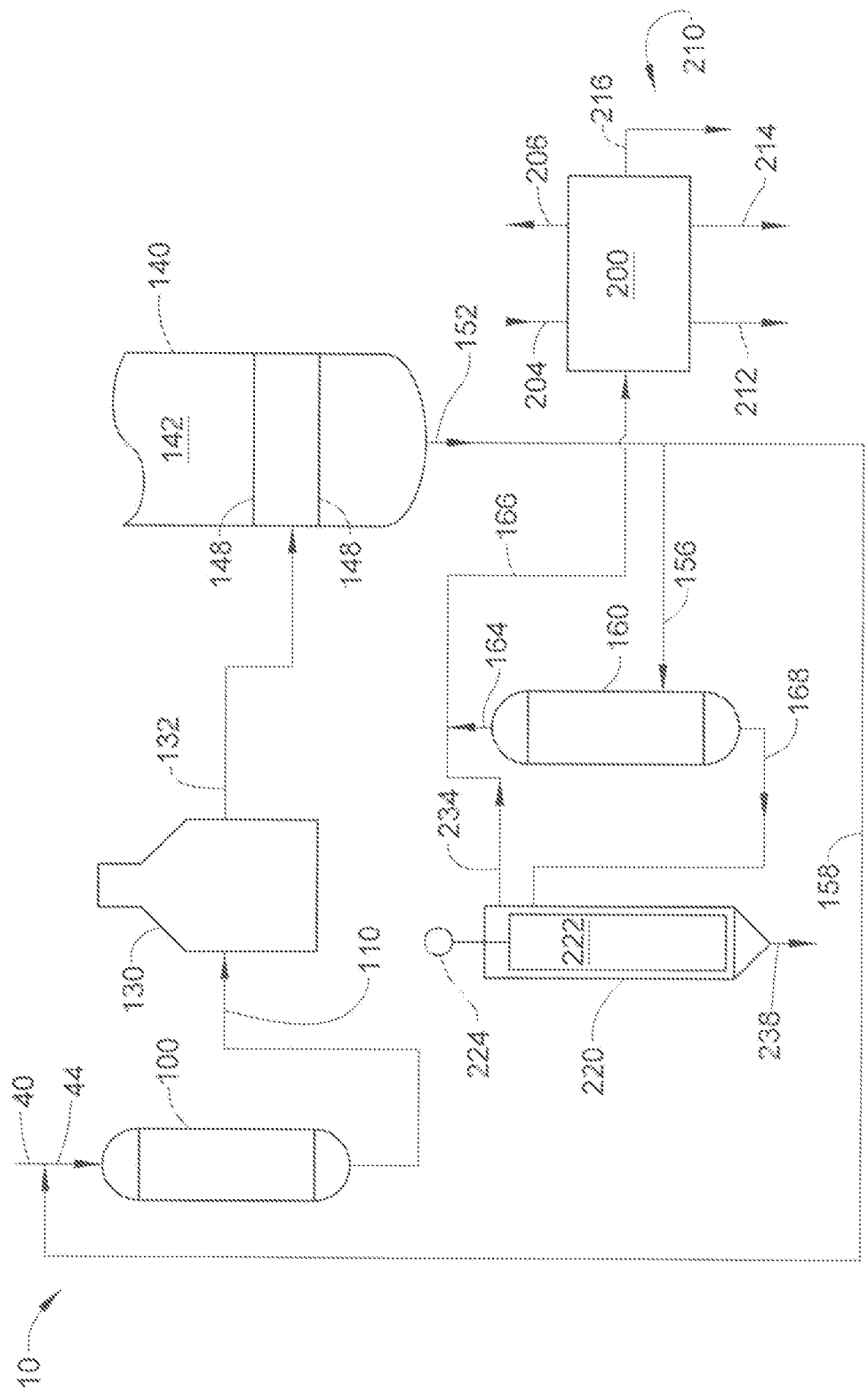
FIG. 1 is a schematic depiction of an exemplary apparatus.

Referring to FIG. 1, one exemplary embodiment of an apparatus 10 is depicted. The apparatus 10 can include a hydroprocessing zone 100, a heater 130, a fractionation zone 140, a separation zone 160, a vacuum zone 200, and a film generating evaporator zone 220. A hydroprocessing feed 40 can be provided to the apparatus 10.

The hydroprocessing feed 40 may be a hydrocarbonaceous oil containing hydrocarbons and/or other organic materials to produce a product containing hydrocarbons and/or other organic materials of lower average boiling point and lower average molecular weight. The hydroprocessing feed 40 may include mineral oils and synthetic oils, e.g., shale oil, and tar sand products, and fractions thereof. An illustrative hydroprocessing feed 40 includes those containing components boiling above about 285° C., such as atmospheric gas oils; vacuum gas oils; deasphalted, vacuum, and atmospheric residua; hydrotreated or mildly hydrocracked residual oils; coker distillates; straight run distillates; solvent-deasphalted oils; pyrolysis-derived oils; high boiling synthetic oils; cycle oils; and cat cracker distillates. One exemplary preferred hydroprocessing feed 40 is a gas oil or other hydrocarbon fraction having at least about 50%, by weight, of its components boiling at temperatures above the end point of the desired product. One exemplary hydroprocessing feed 40 may contain one or more hydrocarbon components boiling above about 285° C., preferably containing at least about 25%, by volume, of the components boiling about 310-about 540° C. The hydroprocessing feed 40 can be combined with a recycle stream 158, as hereinafter described, to form a combined stream 44 provided to the hydroprocessing zone 100. Hydrogen may be added upstream or to the combined stream 44 or directly to the hydroprocessing reactor.

The hydroprocessing zone 100 can include a single reactor or multiple reactors, and undertake processes such as hydrocracking and hydrotreating. The hydroprocessing zone 100 can include a hydrocracking catalyst utilizing amorphous bases or low-level zeolite bases combined with one or more metals of groups 6 and 8-10 of the periodic table acting as hydrogenating metals and promoters. In another embodiment, the catalyst can include any crystalline zeolite cracking base upon which is deposited a minor proportion of a metal of groups 8-10 of the periodic table. The hydrogenating components may also be selected from group 6 of the periodic table for incorporation with a zeolite base. Hydrogenating metals can include one or more of iron, cobalt, nickel, ruthenium, rhodium, palladium, osmium, iridium and platinum, and promoters may include molybdenum and tungsten. The amount of hydrogenating metal in the catalyst can vary within wide ranges, such as about 0.05-about 30%, by weight, based on the weight of the catalyst. In the case of the noble metals, e.g., platinum and palladium, about 0.05-about 2%, by weight, may be used.

The zeolite bases may be referred to as molecular sieves and composed of silica, alumina and one or more exchangeable cations such as sodium, magnesium, calcium, and at least one rare earth metal. They can be further characterized by crystal pores of relatively uniform diameter of about 4-about 14 Angstroms. Suitable zeolites may include mordenite, stilbite, heulandite, ferrierite, dachiardite, chabazite, erionite and faujasite, and B, X, Y and L crystal types, e.g., synthetic faujasite and mordenite. Generally, one exemplary zeolite is a synthetic Y molecular sieve.

The original zeolitic monovalent metals can be ion-exchanged with a polyvalent metal and/or with an ammonium salt followed by heating to decompose the ammonium ions associated with the zeolite, leaving in their place hydrogen ions and/or exchange sites, which may be decationized by further removal of water. Exemplary hydrogen or decationized Y zeolites are disclosed in, e.g., U.S. Pat. No. 3,130,006.

Mixed polyvalent metal-hydrogen zeolites may be prepared by ion-exchanging first with an ammonium salt, then partially back exchanging with a polyvalent metal salt and then calcining. In some cases, the hydrogen forms can be prepared by direct acid treatment of the alkali metal zeolites.

One preferred method for incorporating the hydrogenating metal is contacting the zeolite base material with an aqueous solution of a suitable compound of the desired metal wherein the metal may be present in a cationic form. Following addition of the selected hydrogenating metal or metals, the resulting catalyst powder may be then filtered, dried, pelleted with added lubricants, binders or the like, if desired, and calcined in air at temperatures of, e.g., about 370-about 650° C. in order to activate the catalyst and decompose ammonium ions. Alternatively, the zeolite component may first be pelleted, followed by the addition of the hydrogenating component and activation by calcining. The foregoing catalysts may be employed in undiluted form, or the powdered zeolite catalyst may be mixed and copelleted with other relatively less active catalysts, diluents or binders such as alumina, silica gel, silica-alumina cogels, and activated clays in proportions ranging of about 5-about 90%, by weight, based on the weight of the catalyst. These diluents may be employed as such or they may contain a minor proportion of an added hydrogenating metal of groups 6 and 8-10 of the periodic table.

Additional metal promoted hydrocracking catalysts may also be utilized, which can include aluminophosphate molecular sieves, crystalline chromosilicates, and other crystalline silicates. Such crystalline chromosilicates are disclosed in, e.g., U.S. Pat. No. 4,363,718.

The hydrocracking of a feed with a hydrocracking catalyst can be conducted in the presence of hydrogen and preferably at hydrocracking reactor conditions at a temperature of about 230-about 470° C., a pressure of about 3,450-about 20,690 kPa, an LHSV of about 0.1-about 30 $hr^{-1}$, and a hydrogen circulation rate of about 330-about 25,000 normal $m^3/m^3$. Such feeds and hydroprocessing zones are disclosed in, e.g., U.S. Pat. No. 4,447,315 and U.S. Pat. No. 6,379,535.

A hydroprocessing effluent or fraction 110 can be provided to a heater 130, and heated to any suitable temperature, such as about 140-about 400° C., and provided to a fractionation zone 140. The fractionation zone 140 may include a column 142, a portion of which is depicted, containing one or more trays 148, which can include bubble caps or other suitable vapor/liquid contacting devices. The column 142 can operate with a flash zone temperature of about 340-about 390° C. and a pressure of about 30-about 250 KPa. The heated hydroprocessing fraction 132 can be provided to the column 142 with the lighter components passing upward and lighter products withdrawn further up the column 142, and the heavier components exiting the column 142, such as a bottom stream 152.

The bottom stream 152 can be split into a portion 156 and a recycle stream 158 to the hydroprocessing zone 100. The recycle stream 158 may be combined with the hydroprocessing feed 40 to form the combined stream 44, as described above.

The portion 156 may be provided to the separation zone 160, which can include a drum. The separation zone 160 can be operated at any suitable conditions, to provide a top stream 164 and a bottom stream 168.

The bottom stream 168 from the separation zone 160 can be sent to the film generating evaporator zone 220 including a film generator evaporator. The HPNA compounds can concentrate in the second stream 238 as opposed to being vaporized and included in the vapor stream 234.

A film generating evaporator can promote evaporation of at least a portion of the bottom stream 168 sufficiently quickly to avoid coking. Often, a film generating evaporator includes a moving part for renewing the surface with a portion of the bottom stream 168. Exemplary film generating evaporators are disclosed in, e.g., U.S. Pat. No. 3,316,958; U.S. Pat. No. 4,160,692; and U.S. Pat. No. 4,173,246, and can include a falling film evaporator, a rising film evaporator, a scraped surface evaporator, a thin film evaporator, and a wiped film evaporator.

In a falling film evaporator (may be abbreviated herein as "FFE"), the bottom stream 168 can enter the evaporator at the head and may be evenly distributed into heating tubes. Generally, a thin film enters the FFE and flows downward at boiling temperature and is partially evaporated. A heating medium, such as steam, may be used for heating the outside of the FFE. The bottom stream 168 can flow downward in the FFE and the vaporous hydrocarbons may be separated from heavier hydrocarbons.

Generally, a rising film evaporator (may be abbreviated herein as "RFE") operates on a thermo-siphon principle. The bottom stream 168 can enter a bottom of the RFE heated by a suitable medium provided on the outside of the RFE. As the residue heats, vapor begins to form and ascend. The ascending force of this vapor can cause liquid and vapors to flow upward in parallel flow. At the same time, the production of vapor increases and the liquid may be pressed as a thin film on the walls of the tubes while ascending. Usually, the co-current upward movement against gravity has the beneficial effect of creating a high degree of turbulence in the residue that can promote heat transfer and coke inhibition.

A scraped surface evaporator (may be abbreviated herein as "SSE") can operate similarly as a wiped film evaporator, discussed below. However, an SSE typically endeavors to keep a film of pitch on the heated surface from overheating by frequent removal with a scraper rather than maintain a thin film on the internal heated surface.

A thin film evaporator (may be abbreviated herein as "TFE") may heat the bottom stream 168 on an internal surface of a heated tube until a residue may begin to evaporate. The residue can be maintained as a thin film on the internal surface of the tube by a rotating blade with a fixed clearance. The vapors are then liquefied on the cooler tubes of a condenser.

A wiped film evaporator (may be abbreviated herein as "WFE") is typically different from a TFE in that it uses a hinged blade with minimal clearance from the internal surface to agitate the flowing residue to effect separation. In both TFE and WFE, the bottom stream 168 can enter the unit tangentially above a heated internal tube and may be distributed evenly over an inner circumference of the tube by the rotating blade. The residue can spiral down the wall while bow waves developed by rotor blades may generate highly turbulent flow and optimum heat flux. The residue may evaporate rapidly and vapors can flow either co-currently or counter-currently against the residue. In some exemplary TFE and WFE designs, a residue may be condensed in a condenser located outside but as close to the evaporator as possible. As an example, a short path distillation unit can include a TFE or a WFE that has an internal condenser, or be used instead.

In this exemplary embodiment as depicted, the film generator evaporator zone 220 can include a wiped film evaporator 222 powered by a motor 224. Generally, the wiped film evaporator 222 has a blade vaporizing hydrocarbons applied to a drum. The wiped film evaporator 222 may provide a first stream 234 containing less HPNA compounds than a second stream 238.

The first stream 234 may include one or more C22-C35 hydrocarbons and boil at about 370-about 480° C., and the vapors may be condensed to produce a light and heavy distillate product. Non-condensable vapors can be vented to a suitable destination. The second stream 238 can include non-distillable components such as HPNA compounds, solids and other impurities and may be sold as asphalt blending components or as a supplemental fuel in a cement kiln or steel mill, passed to storage, or routed to fuel oil. The second stream 238 can include one or more C28+ hydrocarbons, and may have a boiling point of at least about 426° C.

The first stream 234 absent some or a substantial amount of HPNA compounds can be routed to the vacuum zone 200, along with the vapor stream 164 from the separation zone 160 to form a combined stream 166. The vacuum zone 200 can include any suitable pumps and vessels to separate one or more hydrocarbon streams 210, such as a light distillate 212, a heavy distillate 214, and an oily condensate 216 by applying vacuum conditions to the combined stream 166. The vacuum zone 200 may receive a steam stream 204 and discharge a vent stream 206 for facilitating vacuum conditions.

Figure 2:
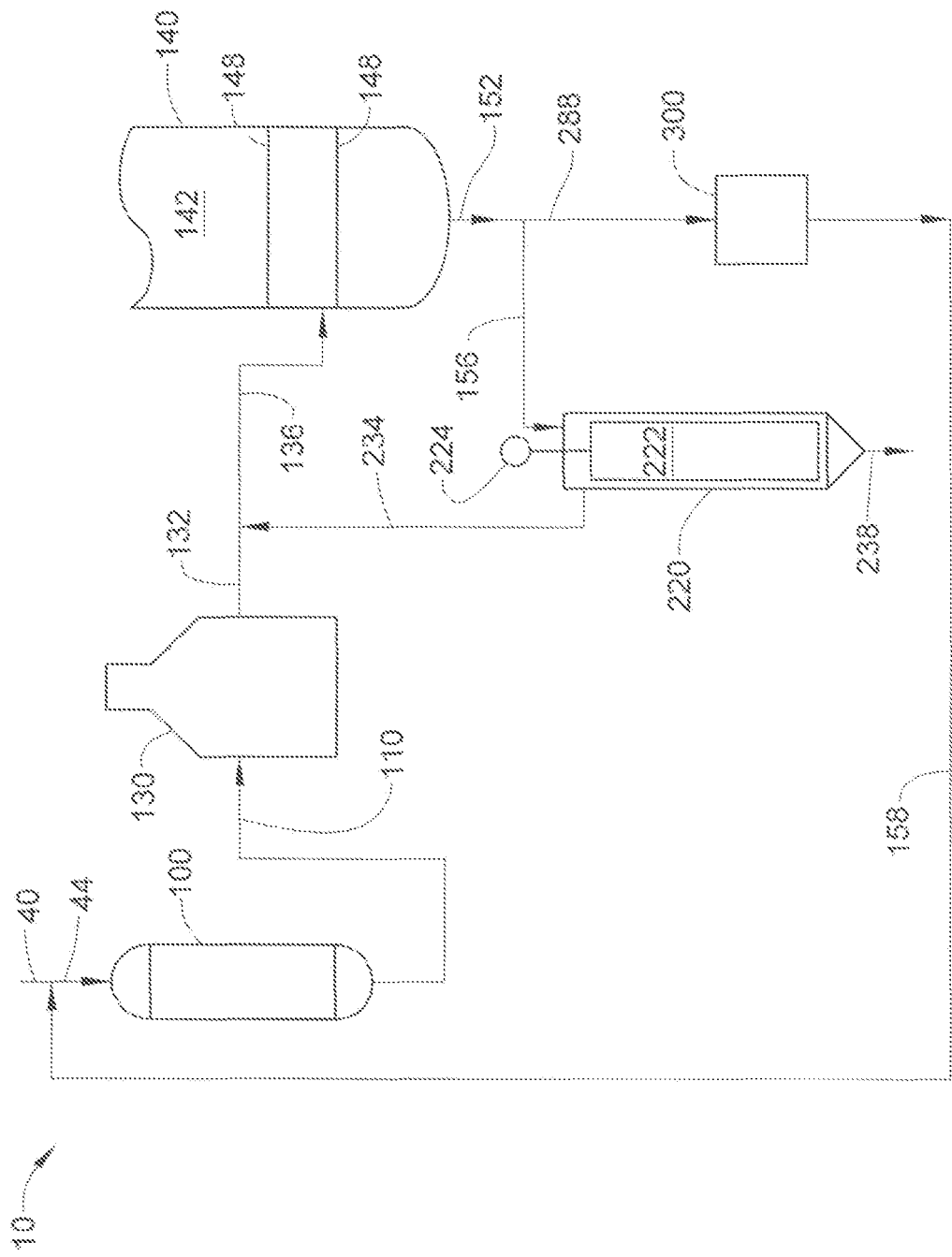
FIG. 2 is a schematic depiction of another embodiment of the exemplary apparatus.

Referring to FIG. 2, another embodiment of the apparatus 10 can include the hydroprocessing zone 100, heater 130, fractionation zone 140, and film generating evaporator zone 220, as described above. In addition, an adsorption zone 300 can be provided. Exemplary adsorption zones are disclosed in, e.g., U.S. Pat. No. 4,447,315.

In the adsorption zone 300, another portion 288 containing HPNA compounds may be contacted with a suitable adsorbent, which may selectively retain the HPNA compounds. Suitable adsorbents may include one or more of a molecular sieve, a silica gel, an activated carbon, an activated alumina, a silica-alumina gel, and a clay. The adsorbent may be installed in the adsorption zone 300 in any suitable manner, such as a fixed bed arrangement. The adsorbent may be installed in one or more vessels and either in series or parallel flow. The flow of the another portion 288 through the adsorption zone 300 is preferably provided with the capability of having one bed in operation while the other bed can be regenerated.

The adsorption zone 300 can be maintained at a pressure from about 170-about 4,300 kPa, a temperature from about 10-about 370° C., and an LHSV from about 0.1-about 500 hr$^{-1}$. The flow of the hydrocarbons through the adsorption zone 300 may be conducted in an upflow, downflow or radial flow manner with the hydrocarbons in the liquid phase. The resulting unconverted hydrocarbon oil having a reduced concentration of HPNA compounds may then be recycled to the hydroprocessing zone 100 for further processing and subsequent conversion to lower boiling hydrocarbons.

In operation, the hydroprocessing feed 40 often is mixed with an unconverted oil stream 158 and the resultant mixture 44 along with a hydrogen-rich vapor can be provided to the hydroprocessing zone 100. The hydroprocessing fraction 110 may be passed through the heater 130 as a heated hydroprocessing fraction 132, as discussed above for the embodiment of FIG. 1. The heated hydroprocessing fraction 132 can be combined with the first stream 234 from the film generating evaporator zone 220 to form a combined stream 136 sent to the fractionation zone 140. The bottom stream 152 obtained from the fractionation zone 140 can be split into the portion 156 and another portion 288. The portion 156 can be sent to the film generating evaporator zone 220 to obtain the first stream 234 and the second stream 238, as discussed above. Another portion 288 can be provided to the adsorption zone 300 for removing HPNA compounds prior to providing the recycle stream 158 for combining with the hydroprocessing feed 40.

Figure 3:
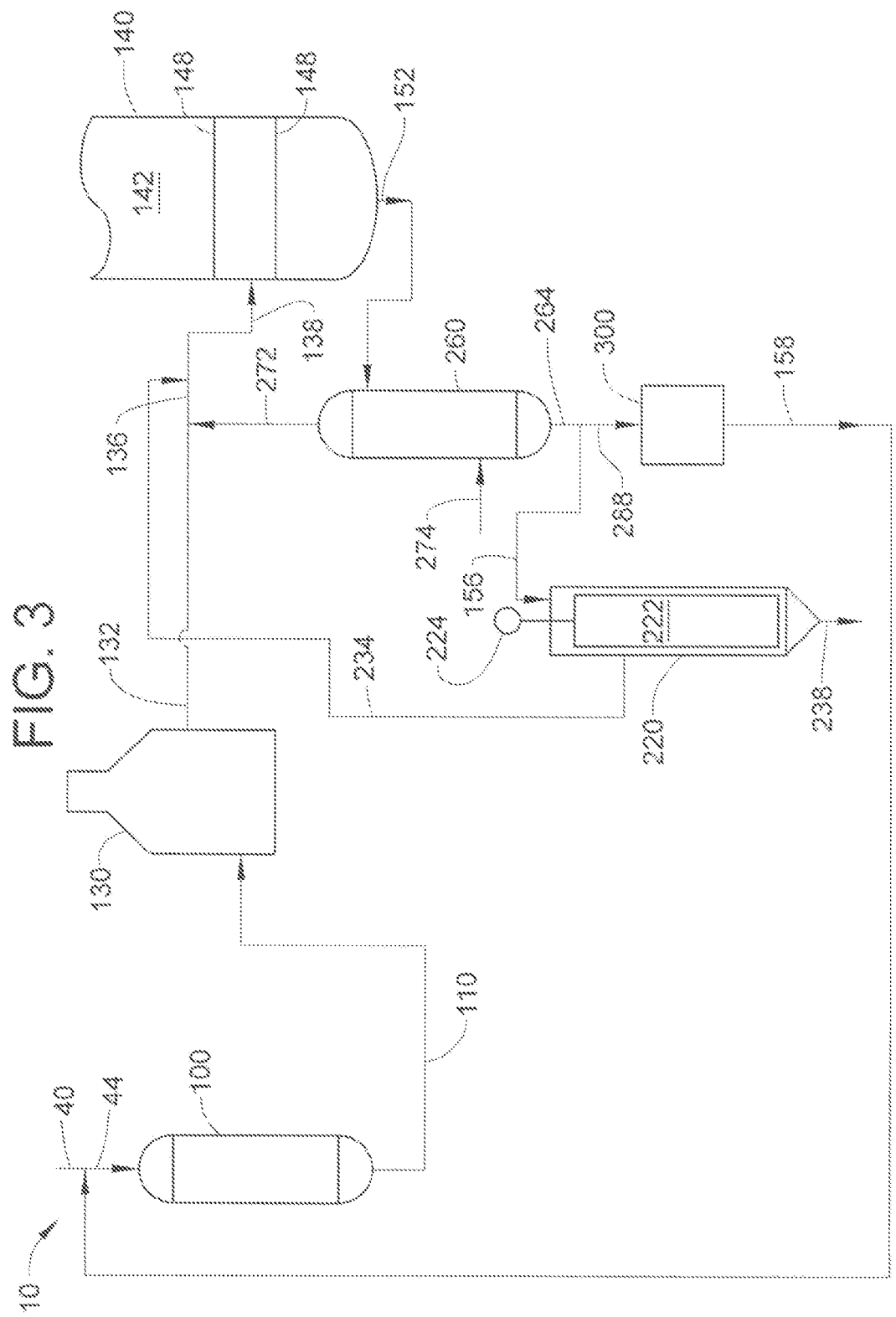
FIG. 3 is a schematic depiction of a further embodiment of the exemplary apparatus.

Referring FIG. 3, a further embodiment is depicted of the apparatus 10. This embodiment can be substantially similar to the embodiment of FIG. 2 with the addition of a stripping zone or vessel 260. The stripping vessel 260 may receive the bottom stream 152 from the fractionation zone 140. The stripping vessel 260 can receive a steam stream 274 for stripping lighter hydrocarbons, such as diesel and lighter compounds, from the bottom stream 152 to improve distillate yields at a temperature about 320-about 430° C. at any suitable rate, such as about 10-about 110 kg/m$^3$. The stripping steam stream 274 can be adjusted to provide the necessary lift of lighter material such that the remaining bottoms liquid may have higher levels of HPNA compounds. At least a portion of the stripped hydrocarbons can exit as the top stream 272 including vapor containing sufficient steam to provide for the stripping requirements of the fractionation zone 140. This steam can aid separation in the fractionation zone 140.

A top stream 272 from the stripping vessel 260 may be separated and combined with the combined stream 136 and the first stream 234 from the film generating evaporator zone 220 to form a combined fractionation feed 138 for the fractionation zone 140. The vapors from the stripping vessel 260 can be routed to the flash zone of the column 142. A first portion 264 from the bottom of the stripping vessel 260 can be split into a portion 156 fed to the film generator evaporator zone 220 and another portion provided to the adsorption zone 300. The film generator evaporator zone 220 can provide the second stream 238 and the adsorption zone 300 can provide the recycle stream 158 combined with the hydroprocessing feed 40.

Figure 4:
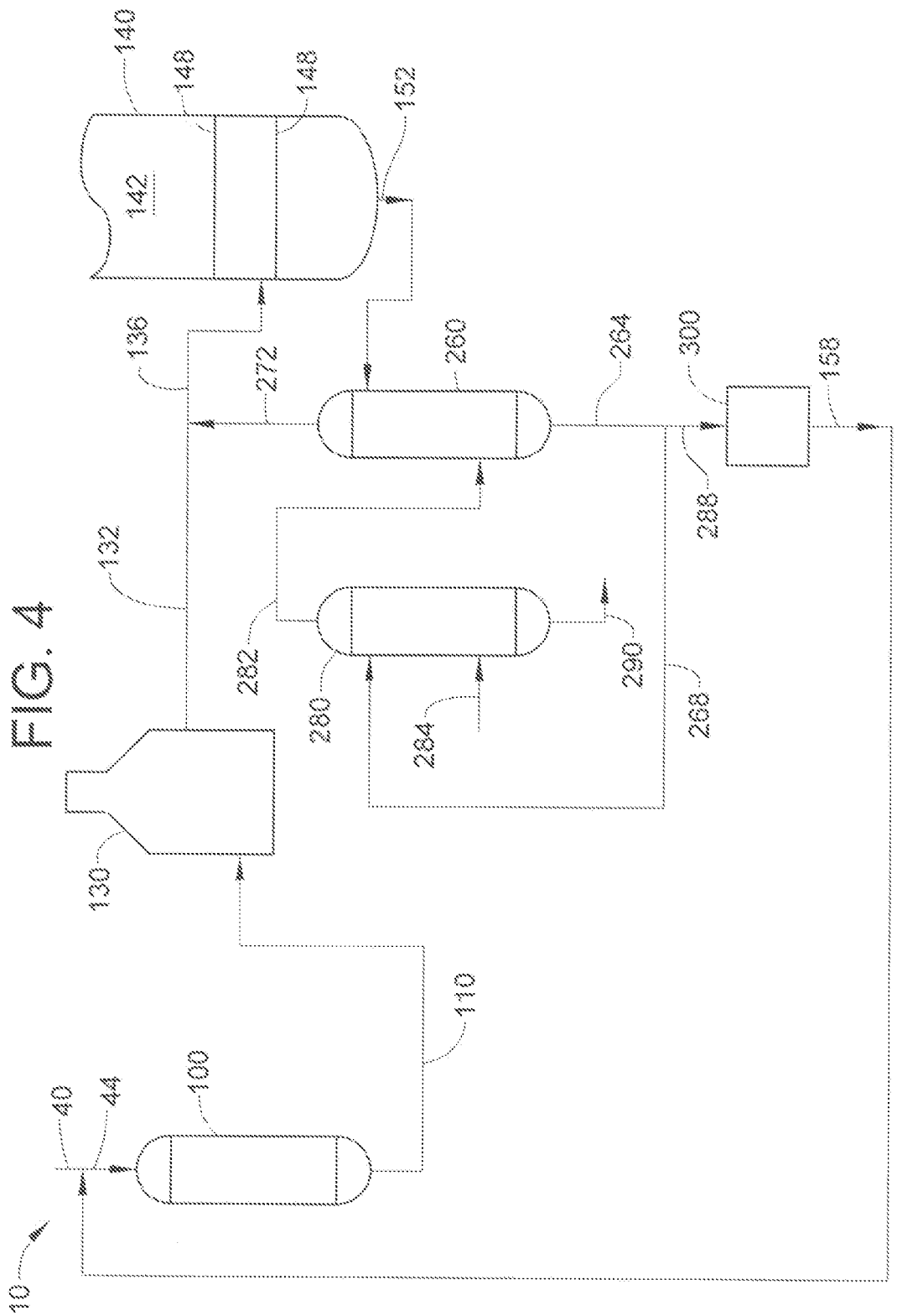
FIG. 4 is a schematic depiction of yet another embodiment of the exemplary apparatus.

Referring to FIG. 4, yet another embodiment of the apparatus 10 is depicted. This exemplary embodiment can be similar to the embodiment as depicted in FIG. 3 with the film generator evaporator zone 220 replaced with another stripping zone 280 in addition to the first stripping zone 260, where each stripping zone 260 and 280 may include a respective stripping vessel. The first portion 264 obtained from the first stripping zone 260 may be split into a portion 268 and another portion 288. The portion 288 can be provided to the adsorption zone 300. The portion 268, which can be about 2-about 10% of the first portion 264, can be routed to the second stripping zone 280. The steam stream 284 may be a superheated steam at a temperature of about 320-about 430° C. at a rate of about 3.5-about 900 kg of steam/m$^3$ of the column 280 feed. The vapor stream 282 from the second stripping zone 280 can be used as the stripping medium for the first stripping zone 260, and the vapors from that vessel may be routed to the flash zone of the column 142.

The portion 268 may be provided to the second stripping zone 280 that can contain a vessel receiving a steam stream 284. The steam stream 284 can strip lighter hydrocarbons in the portion 268. A bottom stream 290 including elevated levels of HPNA compounds can be obtained and disposed of in any suitable manner. A stripping stream 282 may be obtained from the second stripping zone 280 that may be provided to the first stripping zone 260. The first stripping zone 260 can provide the top stream 272 and the first portion 264, as described above.

Figure 5:
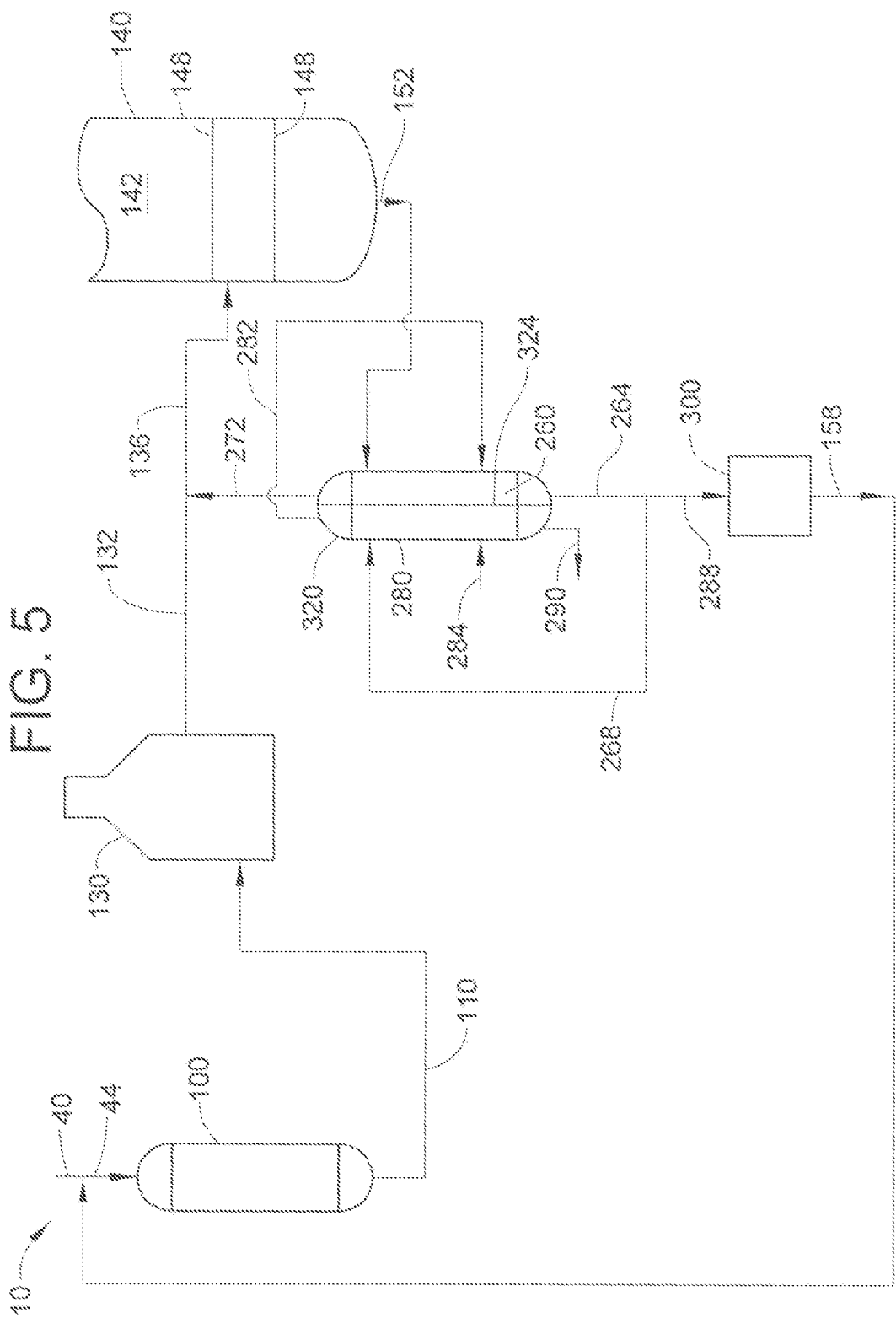
FIG. 5 is a schematic depiction of still another embodiment of the exemplary apparatus.

Referring to FIG. 5, still another embodiment of the apparatus 10 is depicted. This exemplary embodiment can be similar to the embodiment as depicted in FIG. 4 with the first and second stripping zones 260 and 280 combined into a same, single stripping vessel 320 having a dividing wall 324. The bottom stream 152 from the fractionation zone 140 can be provided to one side of the stripping vessel 320. The stripping stream 282 from the other side can strip lighter hydrocarbons that exit as the top stream 272 combined with the heated hydroprocessing fraction 132 provided to the fractionation zone 140. The first portion 264 from the stripping zone 260 can be split into another portion 288 provided to the adsorption zone 300, in turn, providing a recycle stream 158, as discussed above, and the further portion 268. The further portion 268 can be provided to the other side of the stripping vessel 320 that can be stripped with steam stream 284. The bottom stream 290 including an elevated level of HPNA compounds can exit the other side at the bottom, and the stripping stream 282 can be provided to the first side, as discussed above. Thus, the first stripping zone 260 can strip the bottoms liquid from the fractionator, and the other stripping zone 280 can strip to produce the bottom stream 290 with a residue having elevated levels of HPNA compounds.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for treating a hydroprocessing fraction, comprising:
   A) obtaining a bottom stream from a hydroprocessing fractionation zone;
   B) passing at least a portion of the bottom stream to a first stripping zone;
   C) sending a first portion of the stripped bottom stream to an adsorption zone;
   D) sending a second portion of the stripped bottom stream to a second stripping zone; and
   E) recycling a top stream from the first stripping zone to the hydroprocessing fractionation zone.

2. The process according to claim 1, wherein the adsorption zone comprises an activated carbon.

3. The process according to claim 1, wherein the first stripping zone is stripped with a stream obtained from the second stripping zone and the second stripping zone is stripped with steam.

4. The process according to claim 1, wherein the first and second stripping zones are housed in the same vessel.

5. The process according to claim 1, further comprising hydrocracking to obtain the hydroprocessed fraction.

6. The process according to claim 1, further comprising recycling a stream from the adsorption zone to a hydroprocessing zone.

* * * * *